US010015958B2

(12) United States Patent
Murray et al.

(10) Patent No.: US 10,015,958 B2
(45) Date of Patent: Jul. 10, 2018

(54) METHOD OF FREEZING MAKING USE OF A MINERAL NUCLEATOR

(71) Applicants: University of Leeds, Leeds, West Yorkshire (GB); Asymptote Ltd., Cambridge, Cambridgeshire (GB)

(72) Inventors: Benjamin John Murray, Leeds (GB); Thomas Francis Whale, Leeds (GB); James Atkinson, Leeds (GB); George John Morris, Cambridge (GB)

(73) Assignees: University of Leeds, Leeds (GB); Asymptote Ltd, Cambridge (GB)

( * ) Notice: Subject to any disclaimer, the term of this patent is extended or adjusted under 35 U.S.C. 154(b) by 0 days.

(21) Appl. No.: 14/651,366

(22) PCT Filed: Dec. 9, 2013

(86) PCT No.: PCT/GB2013/053239
§ 371 (c)(1),
(2) Date: Jun. 11, 2015

(87) PCT Pub. No.: WO2014/091216
PCT Pub. Date: Jun. 19, 2014

(65) Prior Publication Data
US 2015/0327538 A1   Nov. 19, 2015

(30) Foreign Application Priority Data

Dec. 11, 2012  (GB) .................................. 1222241.0

(51) Int. Cl.
*A01N 1/00* (2006.01)
*A01N 1/02* (2006.01)
*A23G 9/32* (2006.01)

(52) U.S. Cl.
CPC ......... *A01N 1/0221* (2013.01); *A01N 1/0268* (2013.01); *A01N 1/0278* (2013.01);
(Continued)

(58) Field of Classification Search
None
See application file for complete search history.

(56) References Cited

U.S. PATENT DOCUMENTS

| 4,189,401 A | 2/1980 | Louderback |
| 2008/0057040 A1 | 3/2008 | Crook et al. |
| 2013/0260452 A1 | 10/2013 | Toner et al. |

FOREIGN PATENT DOCUMENTS

| CH | 396313 | 7/1965 |
| GB | 907921 | 10/1962 |

(Continued)

OTHER PUBLICATIONS

Fahy, "The Role of Nucleation in Cryopreservation", in Lee et al., Biological Ice Nucleation and Its Applications, pp. 314-336, American Phytopathological Society, 1995.*

(Continued)

*Primary Examiner* — Erin M. Bowers
(74) *Attorney, Agent, or Firm* — Wells St. John P.S.

(57) ABSTRACT

The present invention relates to a method for freezing a water-containing quantity of a biological entity or a formulation in a vessel using a mineral nucleator, to the use of the mineral as a nucleator and to a vessel with the mineral in or on the whole or part of a surface thereof.

18 Claims, 3 Drawing Sheets

(52) U.S. Cl.
CPC ........... *A01N 1/0284* (2013.01); *A23G 9/325* (2013.01); *A23V 2002/00* (2013.01)

(56) References Cited

FOREIGN PATENT DOCUMENTS

| JP | 62-009342 | 2/1987 |
|---|---|---|
| JP | H01107755 | 4/1989 |
| JP | 2005-270006 | 10/2005 |
| JP | 2015-546097 | 3/2017 |
| WO | WO 2005/072080 | 8/2005 |
| WO | WO 2005/118785 | 12/2005 |
| WO | WO 2011/047380 | 4/2011 |
| WO | WO 2011/123693 | 10/2011 |
| WO | PCT/GB2013/053239 | 1/2014 |
| WO | PCT/GB2013/053239 | 6/2015 |

OTHER PUBLICATIONS

Zimmermann et al., J. Geophys. Res. 113: D23204 (2008).*
Kojima et al., Theriogenology 30(6): 1199-1207 (1988).*
Han et al., "Effects of Nanoparticies on the Nucleation and Devitrification Temperatures of Polyol Cryoprotectant Solutions", Microfluidics and Nanofluidics vol. 4, No. 4. Springer, Aug. 3, 2007, Germany, pp. 357-361.
Kojima et al., "Effects of Ice Nucleation by Droplet of Immobilized Silver Iodide on Freezing of Rabbit and Bovine Embryos", Theriogenology vol. 30, No. 6, Dec. 1, 1988, United States, pp. 1199-1207.
Morris et al., "Controlled Ice Nucleation in Cryopreservation—A Review", Cryobiology vol. 66, No. 2, Apr. 2013, United States, pp. 85-92.
Nedava et al., "The Use of High-Dispersion Silicas in Media for Freezing Ram Semen", Sel' Skokhozyaistvennaya Biologiya No. 4, 1992, United States, pp. 20-25.
Deer, et al., "An Introduction to the Rock Forming Minerals", Longman Group Limited, 1966, United Kingdom, 273 pages.
Franks, Felix, "Nucleation of Ice and Its Management in Ecosystems", Philosophical Transactions: Mathematical, Physical and Engineering Sciences, vol. 361, No. 1804, Nucleation Control, 2003, United Kingdom, pp. 557-574.
Hoose, et al., "Heterogeneous Ice Nucleation on Atmospheric Aerosols: A Review of Results from Laboratory Experiments", Atmos. Chem. Phys., 12, 2012, Germany, pp. 9817-9854.
Kasper, et al., "The Freezing Step in Lyophilization: Physicochemical Fundamentals, Freezing Methods and Consequences on Process Performance and Quality Attributes of Biopharmaceuticals", European Journal of Pharmaceutics and Biopharmaceutics 78, 2011, Germany, pp. 248-263.
Konstantinidis, et al.,"Controlled Nucleation in Freeze-drying: Effects on Pore Size in the Dried Product Layer, Mass Transfer Resistance, and Primary Drying Rate", Journal of Pharmaceutical Sciences, vol. 100, No. 8, 2011, United States, pp. 3453-3470.

Lee, et al., "Biological Ice Nucleation and Its Applications", The American Phytopathological Society, 1995, United States, 193 pages.
Massie, et al., "Cryopreservation of Encapsulated Liver Spheroids for a Bioartificial Liver: Reducing Latent Cryoinjury Using an Ice Nucleating Agent", Tissue Engineering: Part C, vol. 17, No. 7, 2011, United States, pp. 765-774.
Murray, et al., "Ice Nucleation by Particles Immersed in Supercooled Cloud Droplets", Chem. Soc. Rev., 2012, 41, United Kingdom, pp. 6519-6554.
Saridakis, et al., "Towards a 'Universal' Nucleant for Protein Crystallization", Trends in Biotechnoogy, vol. 27, No. 2, 2008, United States, pp. 99-106.
Searles, et al., "The Ice Nucleation Temperature Determines the Primary Drying Rate of Lyophilization for Samples Frozen on a Temperature-Controlled Shelf", Journal of Pharmaceutical Sciences, vol. 90, No. 7, 2001, United States, pp. 860-871.
Vonnegut, et al., "Repeated Nucleation of a Supercooled Water Sample that Contains Silver Iodide Particles", Journal of Climate and Applied Meterology, vol. 23, 1984, United States, pp. 486-490.
Whittingham, D.G., "Some Factors Affecting Embryo Storage in Laboratory Animals", in Ciba Foundation Symposium 52—The Freezing of Mammalian Embryos, 1977, United Kingdom, pp. 97-109.
Zimmermann, et al., "Ice Nucleation Properties of the Most Abundant Mineral Dust Phases", Journal of Geophysical Research, vol. 113, D23204, 2008, United States, 11 pages.
Claquin, T., Schultz, M., and Balkanski, Y.J., Modeling the minerology of atmospheric dust sources, J. Geophys. Res., 104, 22243-22256, 1999.
Dymarska, M., Murray, B.J., Sun, L.M., Eastwood, M.L., Knopf, D.A., and Bertram, A.K.: Deposition ice nucleation on soot at temperatures relevant for the lower troposphere, J. Geophys. Res.-Atmos., 111, 2006.
Hoose, C., Lohmann, U., Erdin, R., and Tegen, I.: The global influence of dust mineralogical composition on heterogeneous ice nucleation in mixed-phase clouds, Environ. Res. Lett. 3 (2008) 14 pp.
Kanji, Z.A., Florea, O., and Abbatt, J.P.: Ice formation via deposition nucleation on mineral dust and organics: dependence of onset relative humidity on total particulate surface area, Environ. Res. Lett., 3, 025004, 2008.
Kanji, Z.A. and Abbatt, J.P.D.: Laboratory studies of ice formation via deposition mode nucleation onto mineral dust and n-hexane soot samples. J. Geophys. Res.-Atmos., 111, 2006.
Mason, B.J. and Maybank, J.: Ice-Nucleating Properties of Some Natural Mineral Dusts, Q.J.R. Meteorol. Soc., 84, 235-241, 1958.
Mason, B.J.: Ice-nucleating properties of clay minerals and stony meteorites, Q.J.R. Meteorol. Soc., 86, 552-556, 1960.
Chinese Patent Application No. 201380064752.8 Office Action and English Translation with Search Report dated Aug. 10, 2016, 12 pages.

* cited by examiner

METHOD OF FREEZING MAKING USE OF A MINERAL NUCLEATOR

RELATED PATENT DATA

This application is a 35 U.S.C. § 371 of and claims priority to PCT International Application No. PCT/GB2013/053239 which was filed on 9 Dec. 2013, and was published in English, and claims priority to GB Patent Application No. 1222241.0, which was filed on 11 Dec. 2012, the teachings of which are incorporated herein by reference.

The present invention relates to a method for freezing a water-containing quantity of a biological entity or a formulation in a vessel using a mineral nucleator, to the use of the mineral as a nucleator and to a vessel with the mineral in or on the whole or part of a surface thereof.

There are two related processes for the preservation of biological material. In cryopreservation, the biological material is frozen and stored in the frozen state. In freeze drying (lyophilisation), water is removed from the frozen biological sample which is then stored in the dried state. Freeze drying is also used in (for example) storage of drugs and patterning of solutes.

Cryopreservation is widely employed to maintain long term viability of biological samples for use in medicine, biotechnology and veterinary science. In order to obtain high viability upon thawing it is necessary to add protective compounds (known as cryoprotective additives or cryoprotectants) and cool samples at a controlled rate. With many cell types, it is desirable to induce ice formation by controlled nucleation rather than to allow spontaneous ice nucleation during cooling.

Samples for cryopreservation are generally placed in specialist cryocontainers such as the following:

Straws which are thin walled tubes of 2 to 4 mm diameter and length up to 140 mm with a capacity of 0.2 ml to 0.5 ml;

Cryovials which are wide short tubes of about 12.5 mm diameter and a capacity of 0.5 ml to 5.0 ml;

Flexible bags with a capacity of 5 ml to 1000 ml for the cryopreservation of larger volumes; and Microtitre plates, matrix tubes and other SBS formats employed in robotics and high throughput screening.

A range of equipment is available to freeze straws and cryovials at a controlled rate. These may use liquid nitrogen as a cryogen or be cooled by mechanical refrigeration. Additionally a number of passive cooling devices exist. Some of these devices allow the controlled nucleation of ice within samples which may be carried out manually or automatically.

Following freezing at a controlled rate, samples are held frozen at low temperature (typically the temperature of liquid nitrogen (−196° C.)). At this temperature, the viability of a cell is independent of the period of storage if it survived cooling. When required for use, the samples are thawed rapidly (generally in a water bath maintained at 37° C.) and the cryoprotectant is removed.

Freeze drying (lyophilization) is used extensively in biotechnology, medicine and veterinary science for the long term stabilisation of cells, vaccines, proteins and other bioactive compounds. Freeze drying is also used to generate structured materials such as scaffolds and matrices for application in regenerative medicine (Massie I et al (2011), Tissue Eng Part C Methods. 17:765-774) and in the production of novel ceramics. In the freeze drying process, aqueous samples are placed in specialist containers (typically glass vials) and frozen on a cooled shelf in a freeze drier. Following freezing, the local gas pressure is reduced and ice within the frozen sample sublimates. Following removal of water from the sample, the vial is warmed under vacuum and sealed. The sample may be distributed at ambient temperature and is reconstituted by adding water.

In freeze drying, samples tend to supercool extensively which leads to different ice crystal structures from sample to sample. Ice nucleation at a temperature near to the melting point results in a sample with large ice crystals which sublimate rapidly. In contrast, a sample in which ice nucleation occurs at a temperature remote from the melting point will have small ice crystals and sublimate at a slow rate (Searles J A et al (2001), Journal of Pharmaceutical Sciences 90: 860-871). When processing a large number of samples, the process conditions are usually selected to accommodate the slow drying of the population with the smallest ice crystals resulting in extended processing time and inefficient use of equipment and facilities. The ice nucleation temperature is recognised as a key factor in determining both the processing time and recovery of biological activity (Kasper J C, Friess W (2011), European Journal of Pharmaceutics and Biopharmaceutics 78: 248-263).

The successful recovery of mammalian embryos following conventional cryopreservation is dependent on controlled ice nucleation at a high sub-zero temperature (usually −7° C.). Samples in which ice is allowed to nucleate spontaneously have low recovery due to the formation of intracellular ice as a result of extensive supercooling (Whittingham D G (1977), Ciba Foundation 52. Elsevier Amsterdam Eds K Elliot and J Whelan pp 97-127). The viability of many other cell types including mammalian spermatozoa and stem cells is also increased by controlling ice nucleation. This is generally carried out by cooling the cryocontainer such that the contents are below their melting point and then manually touching the outside of the cryocontainer with a cold implement or mechanically agitating the cryocontainer. This procedure is generally referred to as 'seeding'. The disadvantages of seeding are that it is a manual step which means that relatively few samples can be processed and physical access to the samples is required.

Other physical methods have been proposed to induce nucleation. For example in a freeze drier, the crystallisation of water vapour (snow) which then falls into samples induces nucleation. Recently the Praxair Corporation have introduced a 'pressure shift' process in which samples are pressurised within a freeze drier with argon to 28 psig and then cooled to a desired nucleation temperature. The pressure is then reduced to 1 psig to induce nucleation (Konstantinidis A K et al (2011), Journal of Pharmaceutical Sciences 100: 3453-3470). However this approach is still experimental, costly, difficult to retrofit and not suited to a small freezer drier.

A number of chemical nucleators (sometimes referred to as nucleating catalysts) have been examined for ice nucleation of cryopreservation samples. These nucleators promote a phenomenon referred to as heterogeneous or facilitated nucleation. Examples include crystals of silver iodide, the bacterium *Pseudomonas syringeae* and crystals of cholesterol. The nucleators are added to the sample which is then cooled. When a sufficient level of supercooling is attained within the sample, ice nucleation occurs. This approach allows the processing of large numbers of samples but there are disadvantages relating to their toxicity or potential toxicity or their bacterial or animal origin. Known nucleators are unlikely to be employed with cells for clinical application. Whilst a number of these nucleators induce ice formation at relatively high sub-zero temperatures, it is unlikely that they could be manufactured to standards of Good Manufacturing Practice (GMP) and they may be toxic (Saridakis E et al (2008), Trends in Biotechnology. 27: 99-106).

Some strains of bacteria are capable of nucleating ice at temperatures as high as −2° C. (Vali G. (1995). *Principles of ice nucleation. Biological Ice Nucleation and Its Applications*. R. E. Lee, G. Warren and L. Gusta. St. Paul, Minn., APS press). However the ice nucleating activity of bacteria is highly sensitive to environmental growth conditions and the resulting proteins are heat sensitive. This sensitivity to environmental conditions makes them unsuitable for this application. There are reports of other (non-bacterial) biological materials nucleating ice at high sub-zero temperatures (Henderson-Begg S K. et al (2009). Atmospheric Science Letters 10: 215-219). However the ice nuclei tend to be unstable on heating and remain very poorly characterised. Silver iodide has been shown to catalyse ice formation at very high temperatures (Vonnegut B et al (1984), J. Appl. Meteor. 23(3): 486-490) but cannot be used with samples for clinical application.

Mineral dusts are regarded as relatively inefficient ice nuclei. Review articles which summarise ice nucleation data for solid particles immersed in water droplets quote the highest freezing temperature for mineral dusts of around −15° C. (Hoose C and 0 Möhler (2012), Atmospheric Chemistry and Physics. 12: 9817-9854; and Murray B. J et al (2012), Chemical Society Reviews. 41: 6519-6554).

Scraped surface heat exchangers are used to freeze large volumes of a mixture of water, sugar, dairy products, colours, flavourings and other additives to form ice cream or slush drinks. The scraped surface heat exchanger cools the mixture under high pressure and constant agitation. Nucleation generally occurs spontaneously in a relatively small number of locations. Ice crystals grow continuously and are broken up mechanically to minimise the size of ice crystals present in the finished product. Small ice crystals are regarded as desirable as they give the ice cream a smoother texture than ice cream containing larger ice crystals. However due to its high sugar content, ice cream will tend to partially melt and refreeze when stored at temperatures between −10° C. and −20° C. leading to growth of larger ice crystals.

The present invention seeks to improve freeze processing of water-containing products by deploying a mineral for the controlled nucleation of ice.

Thus viewed from a first aspect the present invention provides a method for freezing a water-containing quantity of a biological entity or a formulation comprising:
  (A) contacting the water-containing quantity with a mineral nucleator in a vessel; and
  (B) cooling the water-containing quantity such that the mineral nucleator serves to promote non-spontaneous formation of ice.

By promoting non-spontaneous formation of ice, the mineral nucleator advantageously provides an element of control over ice nucleation which contributes to preserving the integrity of the biological entity or formulation. This may be useful in processes such as (for example) cryopreservation, freeze drying or food preparation. The element of control may be exerted on the number and size of ice crystals and (for example) allow an increase in the number of ice crystals leading to smaller ice crystals.

Typically in step (A), the mineral nucleator is in contact with the water-containing quantity substantially uniformly throughout. This serves to promote non-spontaneous formation of ice uniformly throughout the water-containing quantity and a greater number of small ice crystal size are formed at the expense of large ice crystals in spite of their lesser stability.

The mineral nucleator may be obtained by processing (eg refinement or concentration) of a mineral source (eg rock, gem or ore) by (for example) one or more physical (eg mechanical) processes such as crushing and gravitational, magnetic or electrical separation or by chemical processes. The mineral nucleator may be a concentrate which is commercial grade or industrial grade. The mineral nucleator may be mineral-rich. In the mineral nucleator, there may be traces of other material present (eg trace minerals such as a clay or calcite or trace non-minerals) which may be endogenous to the mineral source or added as an additive.

The average particle size of the mineral nucleator may be submicron or in the range 1 to 5 μm. Alternatively the mineral nucleator may take the form of beads typically with a millimeter dimension.

Preferably the mineral nucleator is selected from the group consisting of Feldspar, Silica (eg Quartz or Chalcedony such as Jasper), Nepheline, Petalite, Leucite, Sodalite, Cancrinite (eg Cancrinite-Vishnevite), Scapolite, Analcite and Zeolite.

In a preferred embodiment, the mineral nucleator is a framework silicate. Particularly preferably the mineral nucleator is a framework aluminosilicate.

In a preferred embodiment, the mineral nucleator is a Feldspar or Feldsapthoid. In a particularly preferred embodiment, the mineral nucleator is a Feldspar.

A Feldspar is an excellent mineral nucleator and generally exhibits longer lasting activity than other minerals. Without wishing to be bound by theory, the advantages of Feldspar may be attributable to minimal lattice mismatch with ice, low surface charge, low hydrophobicity and/or special nucleation sites (eg defects or cracks).

The Feldspar may be a ternary solid solution of $CaAl_2Si_2O_8$ (anorthite), $NaAlSi_3O_8$ (albite) and $KAlSi_3O_8$ (orthoclase or microcline).

In a particularly preferred embodiment, the mineral is a Feldspar with a predominance of $NaAlSi_3O_8$ and $KAlSi_3O_8$ (ie a predominance of Na and K cations—an alkali Feldspar). The alkali Feldspar may be selected from the group consisting of orthoclase, sanidine, microcline and anorthoclase.

In a more preferred embodiment, the mineral is a Feldspar with a predominance of $KAlSi_3O_8$ (ie a predominance of K cations—potassium Feldspar or K-spar).

In a particularly preferred embodiment, the mineral is a Feldspar with a predominance of $CaAl_2Si_2O_8$ and $NaAlSi_3O_8$ (ie a predominance of Ca and Na cations—a plagioclase Feldspar). The plagioclase Feldspar may be selected from the group consisting of albite, oligoclase, andesine, labradorite, bytownite and anorthite.

In a more preferred embodiment, the mineral is a Feldspar with a predominance of $NaAlSi_3O_8$ (ie a predominance of Na cations).

The water-containing quantity may be a solution, suspension, dispersion, emulsion or colloid of the biological entity or formulation.

Preferably the water-containing quantity is a water-containing quantity of a formulation.

The formulation may be a non-medical formulation.

Preferably the formulation is a medical formulation (eg a pharmaceutical formulation or veterinary formulation).

The formulation may be a pharmaceutical (eg drug), cosmetic, diagnostic agent, coating, dye, pigment, alloy, ceramic, cleaning agent, formulated foodstuff, lubricant, fuel, fertiliser or biocide.

The biocide may be a pesticide (eg a herbicide, insecticide, fungicide, rodenticide or pediculicide).

The water-containing quantity of a formulation may be a metal-containing slurry. The metal-containing slurry may be a mixed metal-containing slurry. In this case, the formulation may be an alloy or ceramic.

Preferably the formulation is a formulated foodstuff. The use of a mineral nucleator leads advantageously to a greater number of smaller ice crystals which gives the foodstuff a desirable texture.

The formulated foodstuff may be a food or beverage.

Preferred formulated foodstuffs are ice cream, yoghurt and slush drink. A particularly preferred formulated foodstuff is ice cream.

Preferably the water-containing quantity is a water-containing quantity of a biological entity.

The biological entity is typically one which has a tendency to lose integrity over time and/or in the presence of environmental stimuli (eg a physical stimulus such as heat or a chemical stimulus such as an enzyme).

The biological entity may derive from a plant or animal (eg from a mammal such as a human).

The biological entity may be a natural foodstuff such as fruit, nuts, herbs or seeds (eg coffee).

Preferably the biological entity is a cell or aggregate of cells (eg a microorganism, microbe, uni-cellular organism, tissue, organ or multi-cellular organism).

By way of example, the cell may be a stem cell, oocyte cell, sperm cell or embryonic cell.

By way of example, the tissue may be skin, tumour, embryonic, testicular or ovarian.

The biological entity may be a protein, enzyme, vaccine, bacterium, virus, protist, protozoan, parasite, spore, seed or fungus.

In a first preferred embodiment, step (A) is:
(A') adding the water-containing quantity to the vessel; and
(A") adding the mineral nucleator in a discrete form to the vessel.

The discrete form may be a pellet, bead, fragment or powder.

The discrete form may be a self-supporting body of the mineral nucleator attached to the vessel or a part thereof (eg a cap or seal). This embodiment allows removal of the mineral nucleator from the sample on thawing.

The discrete form may be added in step (A") in a solution, suspension, dispersion, emulsion or colloid. Typically the mineral nucleator is present in solution, suspension, dispersion, emulsion or colloid in an amount in excess of 0.03 wt %.

The mineral nucleator may be added in step (A") together with a cryoprotectant.

A preferred cryoprotectant contains a plurality of hydroxyl groups (eg a sugar or polyalcohol).

The cryoprotectant may be selected from the group consisting of ethylene glycol, propylene glycol, glycerol, sucrose and DMSO.

In a second preferred embodiment, the mineral nucleator is in or on the whole or part of a surface of the vessel or part thereof such that active nucleation sites of the mineral nucleator are exposed effectively to the water-containing quantity and step (A) is adding the water-containing quantity to the vessel.

In this embodiment, the mineral nucleator may be a constituent of the composition of the vessel (eg impregnated in the vessel). For example, the mineral nucleator may be a constituent introduced during fabrication of the vessel.

The mineral nucleator may be coated on an interior surface of the vessel. Techniques for coating a mineral are known and include plasma-based coating techniques and adhesion impaction.

The vessel may be a sample container or a freezing container such as (for example) a straw, cryovial, bag, microtitre plate or mixing chamber.

During step (B), the vessel may be floated on or immersed in a cryogen (typically liquid nitrogen). Alternatively step (B) is carried out by mechanical refrigeration (eg in a freeze drier or heat exchanger) or by a controlled rate freezer which may be liquid nitrogen-based.

In a preferred embodiment, the method causes the water-containing quantity to freeze at a supercooling of less than 8° C., preferably less than 6° C., more preferably less than 5° C.

Supercooling (also referred to as undercooling) is the temperature of a liquid below the melting point of the solution. For example at −5° C., water would be supercooled by 5° C. whilst a 10% glycerol solution (melting point −2° C.) would be supercooled by 3° C.

Step (B) may proceed to a temperature below −130° C., preferably to a temperature below −150° C., particularly preferably to a temperature of about −196° C.

Step (B) may be carried out incrementally (eg stepwise or continuously). Typically step (B) is carried out continuously at a rate in the range 1 to 2° C./min.

The method may further comprise:
(C) dehydrating the water-containing quantity of the biological entity or formulation.

Step (C) may be carried out by sublimation. Sublimation may be induced by applying a reduction in pressure (eg a partial vacuum) to the vessel.

Viewed from a further aspect the present invention provides the use of a mineral as a nucleator in freezing a water-containing quantity of a biological entity or a formulation in a vessel.

Preferably in the use according to the invention the mineral is in a discrete form.

Preferably in the use according to the invention the mineral is in or on the whole or part of a surface of the vessel or a part thereof.

Viewed from a yet further aspect the present invention provides a vessel with a mineral nucleator in or on the whole or part of a surface thereof or a part thereof.

The vessel may be as hereinbefore defined.

Viewed from a still yet further aspect the present invention provides an aqueous solution, suspension, dispersion, emulsion or colloid comprising a mineral nucleator as hereinbefore defined and a cryoprotectant.

The cryoprotectant may be as hereinbefore defined.

Various embodiments of the invention will now be described in a non-limitative sense only with reference to the following Examples and Figures in which.

Figure 3:
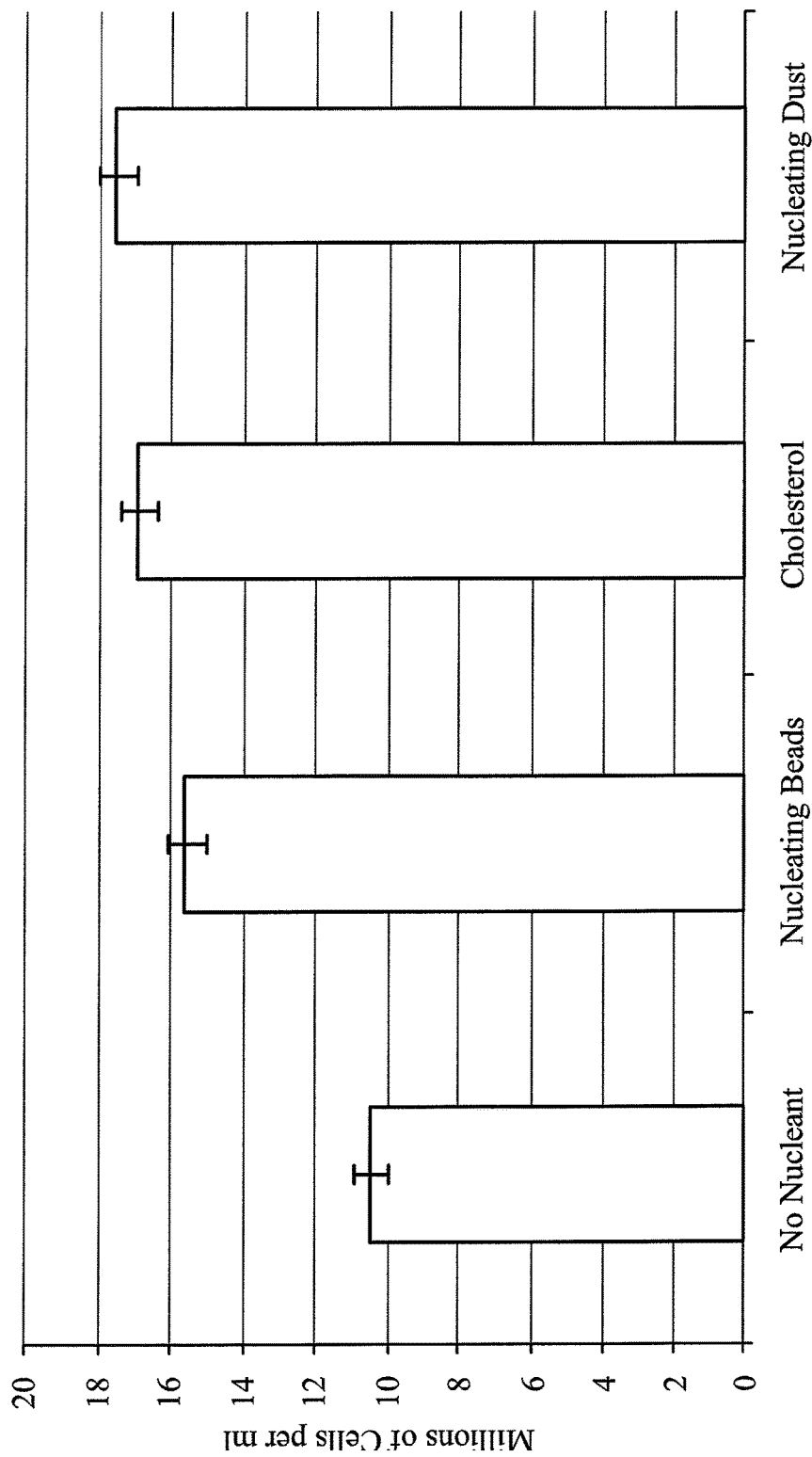
Figure 4:
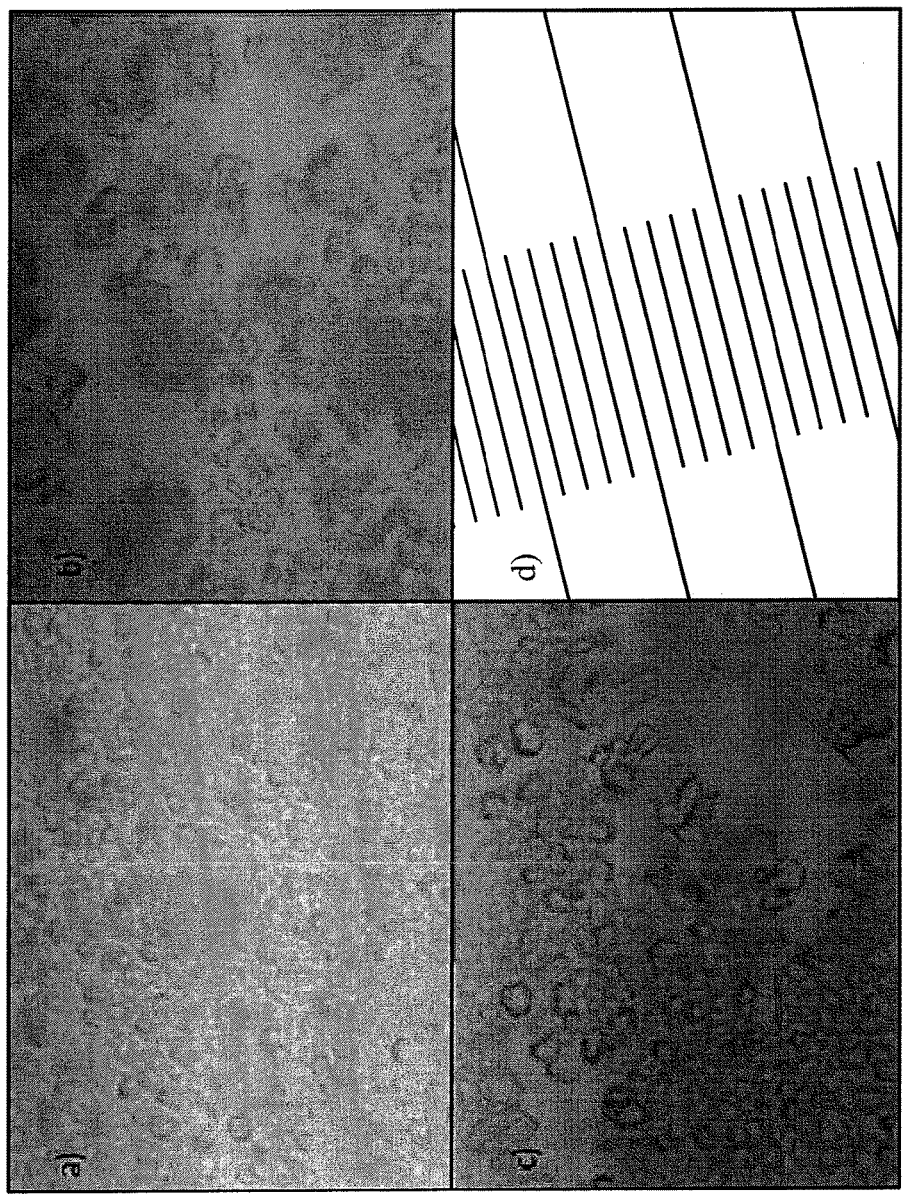

FIG. 3 shows viability data for multicellular liver spheroids encapsulated in alginate after cryopreservation was carried out using a slow-cooling method (a) without nucleator, (b) with cholesterol as a standard nucleator, (c) with Feldspar as a dust (1 μm to 5 μm diameter) and (d) with Feldspar as a bead (6 mm diameter); and FIG. 4 shows (a) ice cream treated with SnoMax®, b) untreated ice cream, c) ice cream treated with K-Feldspar and d) a micrometer at the same magnification as the three samples. The small graduations are 10 μm apart.

EXAMPLE 1—NUCLEATION EXPERIMENTS IN CRYOVIALS

Experiments were carried out in cryovials (Thermo Fisher) placed in an MF2000 prototype electrically powered controlled rate freezer (Asymptote Ltd, Cambridge, UK). The vials were cooled from room temperature down to 4° C. at a rate of 2° C. per minute, then held at 4° C. for 5 minutes and then cooled at 1° C. per minute until nucleation occurred. Nucleation was registered by a T-type thermocouple in each vial and noting the temperature at which the heat of fusion was released. Table 1 shows the average nucleating temperatures of a range of Feldspar materials placed in different solutions of water.

TABLE 1

| Nucleator | Liquid | Average temperature of nucleation, ° C. | Standard deviation of nucleation temperature, ° C. |
|---|---|---|---|
| None (thermocouples) | 10% glycerol in water | −9.74 | 1.10 |
| One or two grains of Forshammer Feldspar in each vial (average weight 0.04 grammes) | 10% glycerol in water | −7.17 | 2.10 |
| 0.060% wt BCS-CRM 376/1 Potash Feldspar | 10% glycerol in water | −7.02 | 0.96 |
| 0.030% wt BCS-CRM 376/1 Potash Feldspar | 10% glycerol in water | −6.93 | 1.24 |
| None (thermocouples) | De-ionised water | −9.08 | 1.98 |
| 0.030% wt BCS-CRM 376/1 Potash Feldspar | De-ionised water | −7.24 | 1.96 |
| 0.060% wt BCS-CRM 376/1 Potash Feldspar | De-ionised water | −6.27 | 1.58 |
| One or two grains of Forshammer Feldspar in each vial (average weight 0.04 grammes) | De-ionised water | −5.71 | 2.48 |
| One bead of feldspar in each vial, 6 mm diameter | De-ionised water | −4.40 | 1.44 |

EXAMPLE 2—NUCLEATION EXPERIMENTS IN STRAWS

Experiments were carried out in straws for cryopreservation of sperm cells. The straws contained PVA (polyvinyl acetate) in one end enclosed between two cotton 'plugs'. The PVA was emptied out from the straw and replaced with the mineral nucleator in powder form. The straws were placed in an EF600 electrically powered controlled rate freezer (Asymptote Ltd, Cambridge, UK) and cooled from room temperature down to 4° C. at a rate of 2° C. per minute, then held at 4° C. for 5 minutes and then cooled at 1° C. per minute until nucleation occurred. Nucleation was registered by a T-type thermocouple in each straw at the opposite end to the nucleator and noting the temperature at which the heat of fusion was released.

Figure 1:
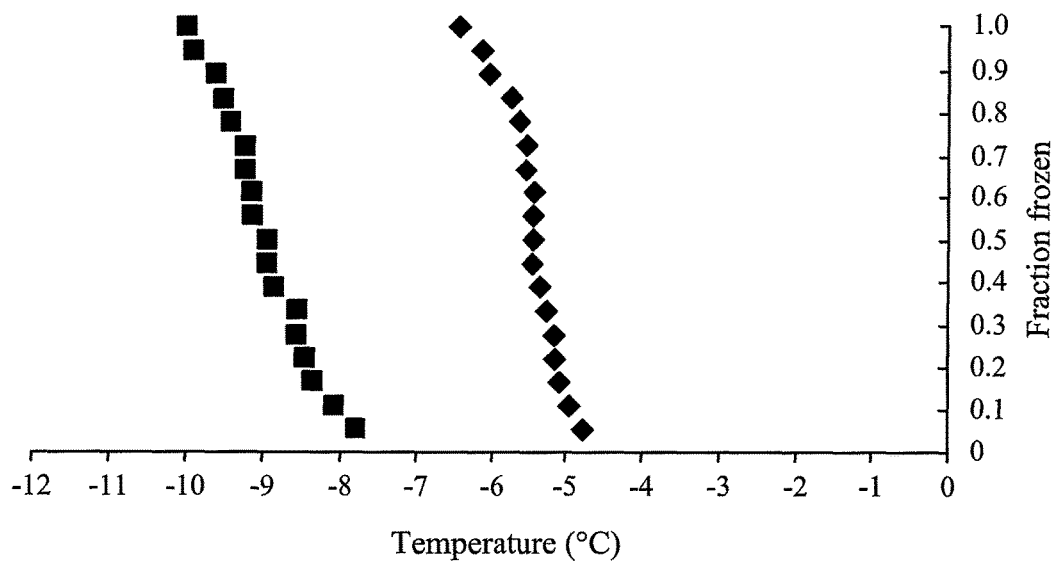
FIG. 1 shows the fraction of straws filled with pure water frozen as a function of temperature with and without the nucleator BCS-CRM 376/1 Potash Feldspar during a 1° C./min cooling ramp (diamonds are straws with Feldspar and squares are those without)

FIG. 1 shows the fraction of straws filled with pure water frozen as a function of temperature with and without the nucleator BCS-CRM 376/1 Potash Feldspar during the 1° C./min cooling ramp (blue diamonds are straws with feldspar and red squares are those without). In this case the freezing temperature was determined by calibrating the relationship between the internal temperature of the straws and the indicated temperature of the EF600 freezer and recording the temperature indicated at the point of freezing. Table 2 shows the average nucleating temperatures with and without the stated nucleators.

TABLE 2

| Nucleator | Liquid | Average temperature of nucleation, ° C. | Standard deviation of nucleation temperature, ° C. |
|---|---|---|---|
| None (thermocouples) | De-ionised water | −9.21 | 1.77 |
| BCS-CRM 376/1 Potash Feldspar | De-ionised water | −6.09 | 1.94 |
| Silica 22 | De-ionised water | −7.41 | 1.17 |

Figure 2:
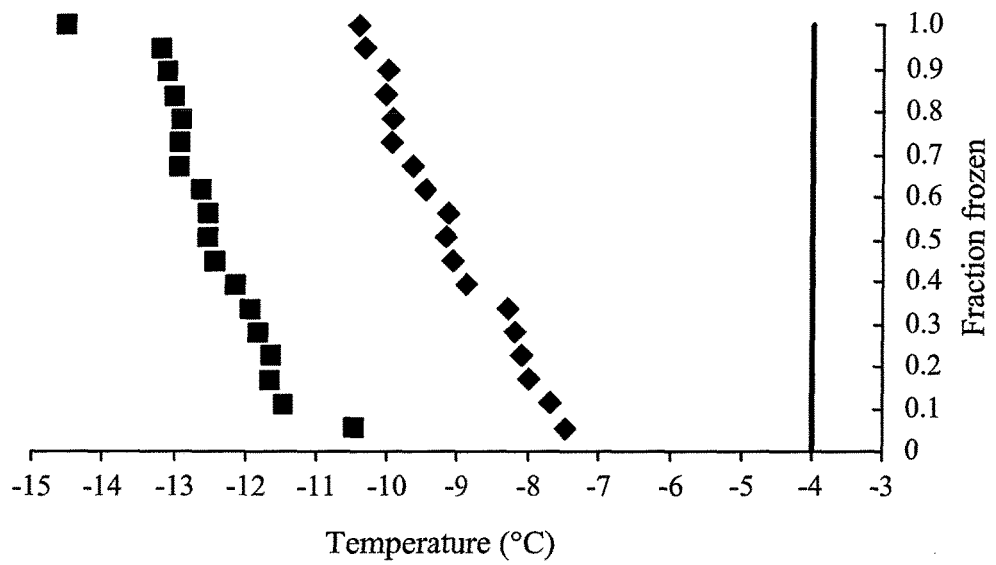
FIG. 2 shows the fraction of straws filled with 10% v/v ethylene glycol frozen as a function of temperature with and without the nucleator BCS-CRM 376/1 Potash Feldspar during a 1° C./min cooling ramp (diamonds are straws with Feldspar and squares are those without. The black line indicates the melting temperature of the liquid frozen)

The experiment was repeated for ethylene glycol in place of pure water. FIG. 2 shows the fraction of straws filled with 10% v/v ethylene glycol frozen as a function of temperature with and without the nucleator BCS-CRM 376/1 Potash Feldspar during the 1° C./min cooling ramp (blue diamonds are straws with Feldspar and red squares are those without). The black line indicates the melting temperature of the liquid frozen. Freezing temperature was determined as described above.

EXAMPLE 3—STABILITY IN SOLUTION

Different preparations of Feldspar were prepared and tested as in Example 1 then left in a consumer grade refrigerator for two weeks and finally tested again using the same experimental protocol. Table 3 shows the average nucleation temperatures for first and second runs of the different Feldspar solutions.

TABLE 3

| Nucleator | Liquid | Average temperature of nucleation ° C., first run | Average temperature of nucleation ° C., second run |
|---|---|---|---|
| 0.060% wt BCS-CRM 376/1 Potash Feldspar | De-ionised water | −6.27 | −7.65 |
| 0.030% wt BCS-CRM 376/1 Potash Feldspar | De-ionised water | −7.24 | −8.21 |
| 0.060% wt BCS-CRM 376/1 Potash Feldspar | 10% glycerol in water | −7.02 | −6.88 |

TABLE 3-continued

| Nucleator | Liquid | Average temperature of nucleation ° C., first run | Average temperature of nucleation ° C., second run |
|---|---|---|---|
| 0.030% wt BCS-CRM 376/1 Potash Feldspar | 10% glycerol in water | −6.93 | −7.42 |

EXAMPLE 4—VIABILITY DATA

An experiment was carried out 72 hours post thaw to determine recovery of multicellular liver spheroids encapsulated in alginate. Viable cell numbers were measured using metabolic vital dyes (flourescein diacetate and propidium iodide) Cryopreservation was carried out using a slow-cooling method with 12% DMSO as cryoprotectant. Samples were cooled (a) without nucleator, (b) with cholesterol as a standard nucleator, (c) with Feldspar as a dust (1 μm to 5 μm diameter) and (d) with feldspar as a bead (6 mm diameter). The results are shown in FIG. 3.

EXAMPLE 5—ICE CREAM CRYSTAL SIZES

To demonstrate the effectiveness of a mineral powder for reducing the size of crystals in liquid food products, experiments were performed using a home ice cream maker and commercially available vanilla Haagen-Daz® ice cream. Experiments were conducted using 500 ml pure melted ice cream, 500 ml melted ice cream mixed with 3 grains of dissolved Snomax® and 500 ml melted ice cream mixed with 1.2 g of powdered K-Feldspar dispersed in 10 ml of water. All three samples were placed in the ice cream maker at a starting temperature of approximately 15° C. and the ice cream maker switched on. The ice cream maker cooled the ice cream down to approximately −20° C. under constant stirring. The ice cream was then quickly transferred to a plastic vessel and placed in a freezer at −18° C. where it was left for 36 hours. At all points great care was taken to prevent cross contamination of ice cream samples.

After this 36 hour period the ice cream was recovered from the freezer and a small amount placed between two microscope slides precooled to −35° C. The slides were then placed onto a transmission microscope equipped with a liquid nitrogen cooled coldstage. FIG. 4 shows typical pictures of the ice crystals in each ice cream sample. The mean size of ice crystals formed in untreated ice cream was determined to be 27±11 μm. In ice cream treated with Snomax® the mean size was found to be 12±3 μm and in ice cream treated with K-Feldspar the mean size was found to be 14±5 μm.

The invention claimed is:

1. A method for freezing a water-containing quantity of a biological entity or a formulation comprising:
contacting the water-containing quantity of the biological entity or formulation with a framework silicate in a vessel to form a solution; and
freezing the solution at a supercooling temperature between 0° C. and 8° C. in the vessel, wherein the framework silicate promotes the non-spontaneous formation of ice at a supercooling temperature between 0° C. and 8° C.

2. A method as claimed in claim 1 wherein the framework silicate is selected from the group consisting of Feldspar, Silica, Nepheline, Petalite, Leucite, Sodalite, Cancrinite, Scapolite, Analcite and Zeolite.

3. A method as claimed in claim 1 wherein the framework silicate is a framework aluminosilicate.

4. A method as claimed in claim 1 wherein the framework silicate is a Feldspar or Feldsapthoid.

5. A method as claimed in claim 1 wherein the framework silicate is a Feldspar.

6. A method as claimed in claim 1 wherein the framework silicate is a Feldspar with a predominance of $NaAlSi_3O_8$ and $KAlSi_3O_8$.

7. A method as claimed in claim 1 wherein the framework silicate is a Feldspar with a predominance of $KAlSi_3O_8$.

8. A method as claimed in claim 1 wherein the framework silicate is a Feldspar with a predominance of $CaAl_2Si_2O_8$ and $NaAlSi_3O_8$.

9. A method as claimed in claim 1 wherein the framework silicate is a Feldspar with a predominance of $NaAlSi_3O_8$.

10. A method as claimed in claim 1 wherein the water-containing quantity is a water-containing quantity of a medical formulation.

11. A method as claimed in claim 1 wherein the water-containing quantity is a water-containing quantity of a formulated foodstuff.

12. A method as claimed in claim 1 wherein the water-containing quantity is a water-containing quantity of a biological entity.

13. A method as claimed in claim 12 wherein the biological entity is a cell or aggregate of cells.

14. A method as claimed in claim 1 wherein the contacting the water-containing quantity with a framework silicate in a vessel comprises:
adding the water-containing quantity to the vessel; and
adding the framework silicate in a discrete form to the vessel.

15. A method as claimed in claim 1 wherein the framework silicate is in or on the whole or part of a surface of the vessel or part thereof such that active nucleation sites of the framework silicate are exposed effectively to the water-containing quantity and the contacting the water-containing quantity with a framework silicate in a vessel comprises adding the water-containing quantity to the vessel.

16. A method for freezing a water-containing quantity of a biological entity or a formulation comprising:
forming a solution comprising the water-containing quantity of the biological entity or formulation, and a framework silicate;
freezing the solution at a supercooling temperature between 0° C. and 8° C.; and
during the freezing, promoting the non-spontaneous formation of ice at the supercooling temperature between 0° C. and 8° C.

17. The method of claim 16 wherein the framework silicate comprises one or more of Feldspar, Silica, Nepheline, Petalite, Leucite, Sodalite, Cancrinite, Scapolite, Analcite and/or Zeolite.

18. The method of claim 16 wherein the forming the solution comprises:
adding the water-containing quantity to a vessel; and
adding the framework silicate in a discrete form to the vessel.

* * * * *

UNITED STATES PATENT AND TRADEMARK OFFICE
CERTIFICATE OF CORRECTION

PATENT NO. : 10,015,958 B2
APPLICATION NO. : 14/651366
DATED : July 10, 2018
INVENTOR(S) : Benjamin John Murray et al.

It is certified that error appears in the above-identified patent and that said Letters Patent is hereby corrected as shown below:

On the Title Page

(56) References Cited – Replace "Han et al., "Effects of Nanoparticies on the Nucleation and Devitrification Temperatures of Polyol Cryoprotectant Solutions", Microfluidics and Nanofluidics vol. 4, No. 4. Springer, Aug. 3, 2007, Germany, pp. 357-361." with --"Han et al., "Effects of Nanoparticles on the Nucleation and Devitrification Temperatures of Polyol Cryoprotectant Solutions", Microfluidics and Nanofluidics vol. 4, No. 4. Springer, Aug. 3, 2007, Germany, pp. 357-361.--

(56) References Cited – Replace "Saridakis, et al., "Towards a 'Universal' Nucleant for Protein Crystallization", Trends in Biotechnoogy, vol. 27, No. 2, 2008, United States, pp. 99-106." with --"Saridakis, et al., "Towards a 'Universal' Nucleant for Protein Crystallization", Trends in Biotechnology, vol. 27, No. 2, 2008, United States, pp. 99-106.--

Signed and Sealed this
Thirtieth Day of October, 2018

Andrei Iancu
*Director of the United States Patent and Trademark Office*